(12) United States Patent
Pahls et al.

(10) Patent No.: US 10,932,939 B1
(45) Date of Patent: Mar. 2, 2021

(54) GLOBAL OSTEOARTHRITIS KNEE BRACE

(71) Applicant: WEBER ORTHOPEDIC, L.P., Santa Paula, CA (US)

(72) Inventors: Dan Pahls, Honesdale, PA (US); Martha Ortega, Oxnard, CA (US); John Hely, Roanoke, TX (US); David Cormier, Oxnard, CA (US); Kelly Nolan, DFW Airport, TX (US); Jim Buckhout, DFW Airport, TX (US); Jeremy Schillig, DFW Airport, TX (US)

(73) Assignee: Weber Orthopedic, L.P., Santa Paula, CA (US)

( * ) Notice: Subject to any disclaimer, the term of this patent is extended or adjusted under 35 U.S.C. 154(b) by 193 days.

(21) Appl. No.: 16/278,634

(22) Filed: Feb. 18, 2019

Related U.S. Application Data (63) Continuation-in-part of application No. 14/869,946, filed on Sep. 29, 2015, now Pat. No. 10,206,804.

(60) Provisional application No. 62/057,131, filed on Sep. 29, 2014.

(51) Int. Cl.
*A61F 5/01* (2006.01)

(52) U.S. Cl.
CPC .......... *A61F 5/0109* (2013.01); *A61F 5/0123* (2013.01); *A61F 5/0106* (2013.01); *A61F 2005/0137* (2013.01); *A61F 2005/0172* (2013.01); *A61F 2005/0176* (2013.01)

(58) Field of Classification Search
CPC .... A61F 5/0106; A61F 5/0109; A61F 5/0123; A61F 2005/0172; A61F 2005/0174; A61F 2005/0176

USPC ..................................... 602/16, 26
See application file for complete search history.

(56) References Cited

U.S. PATENT DOCUMENTS

| 5,626,557 | A | 5/1997 | Mann |
| 5,759,167 | A | 6/1998 | Shields, Jr. et al. |
| 6,527,733 | B1* | 3/2003 | Ceriani ............... A61F 5/0123 602/16 |
| 7,201,728 | B2 | 4/2007 | Sterling |
| 7,217,249 | B2 | 5/2007 | Scott |
| 7,862,528 | B2 | 1/2011 | Scott |
| 7,867,183 | B2 | 1/2011 | Kazmierczak et al. |
| 7,963,933 | B2 | 6/2011 | Nace |
| 8,333,723 | B2 | 12/2012 | Hunter et al. |
| 10,206,804 | B1* | 2/2019 | Pahls ................... A61F 5/0109 |

(Continued)

OTHER PUBLICATIONS

Photograph of 1994 Kinetic Stabilizer using lateral pulls.

*Primary Examiner* — Keri J Nelson
(74) *Attorney, Agent, or Firm* — Paul Y. Feng; One LLP (57) ABSTRACT

A global osteoarthritis knee brace or orthopedic support includes a flexible, elastic sleeve having a tubular shape with a patella opening at an anterior surface with slits on either side of the opening. The brace includes a first pair of rigid longitudinal stiffeners pivoted therebetween at a hinge that is disposed at the lateral or medial side of the sleeve. The brace further includes an adjustable patella support having elongated strips at the ends thereof, wherein the patella support is positioned in the interior of the sleeve proximate with the patella opening, where the elongated strips pass from the interior of the sleeve through the slits to the exterior of the sleeve, and extend upward to be anchored to the sleeve. The wearer pulling on the elongated strips adjusts the patella support to lift the patella.

18 Claims, 5 Drawing Sheets

(56) References Cited

U.S. PATENT DOCUMENTS

| | | |
|---|---|---|
| 2012/0157902 A1 | 6/2012 | Castillo et al. |
| 2012/0220910 A1 | 8/2012 | Gaylord et al. |
| 2013/0178772 A1 | 7/2013 | Oaks et al. |
| 2013/0331753 A1 | 12/2013 | Farrow et al. |
| 2015/0290014 A1 | 10/2015 | Anglada et al. |

* cited by examiner

GLOBAL OSTEOARTHRITIS KNEE BRACE

CROSS-REFERENCE TO RELATED APPLICATIONS

This application is a Continuation-In-Part of co-pending application Ser. No. 14/869,946, filed Sep. 29, 2015, which claims priority to provisional application No. 62/057,131, filed Sep. 29, 2014, the entire contents of which are incorporated by reference.

FIELD OF THE INVENTION

The present invention relates to an orthopedic brace. In particular, the present invention relates to a global osteoarthritis knee brace.

BACKGROUND

Osteoarthritis is caused by cartilage in a person's knees breaking down over time due to age, accumulated physical strain, etc. The loss of cushioning cartilage in the joint allows bone-on-bone contact, leading to chronic pain. Often, the afflicted knee joint is highly swollen and enlarged. One popular treatment is having the osteoarthritis sufferer wear a knee brace to reduce the knee joint pain and to provide him or her with mobility.

SUMMARY OF THE INVENTION

The present invention in a preferred embodiment is directed to an osteoarthritis knee brace, comprising a flexible and elastic sleeve having a tubular shape with an interior and exterior, lateral and medial surfaces, the sleeve further having a patella opening at an anterior surface, and a plurality of slits on either side of the opening. The brace includes a first pair of rigid longitudinal stiffeners pivoted therebetween at a hinge that is disposed at the lateral surface of the sleeve. A second pair of rigid longitudinal stiffeners pivoted therebetween at a hinge, is disposed at the medial surface of the sleeve. The brace further includes an adjustable, flexible patella support having elongated strips at the ends thereof, wherein the patella support is positioned in the interior of the sleeve proximate with the patella opening, and wherein the elongated strips pass from the interior of the sleeve through the slits to the exterior of the sleeve, and further extend upward to be adjustably anchored to the sleeve, and wherein the wearer pulling on the elongated strips adjusts the patella support to lift the patella. A strap extends circumferentially around the outside of the sleeve. Preferably, the patella support includes a crescent shape and is elastic, and may include padding engaging the patella.

In an alternative embodiment, the osteoarthritis knee brace for lifting a wearer's patella comprises a flexible and elastic sleeve having a tubular shape with an interior and exterior, lateral and medial surfaces, the sleeve further having a patella opening at an anterior surface, and a plurality of slits. The sleeve includes an anterior split opening either above or below the patella opening, or both, which feature accommodates patients with a conical leg, and reduces the different sizes a retailer or clinic must stock in inventory. The sleeve has at least one hinge having upper and lower struts that is fitted to the sleeve at either the medial side, lateral side, or both. The brace includes a flexible patella support having elongated strips extending therefrom, wherein the patella support is positioned in the interior of the sleeve beneath with the patella opening, wherein the elongated strips pass from the interior of the sleeve through the slits to the exterior of the sleeve, and further extend upward to be adjustably anchored to the sleeve above the patella opening. When the wearer pulls on the elongated strips, the tension adjusts the patella support to lift the patella. One or more straps are provided and extend circumferentially around the outside of the sleeve.

The upper strut, the lower strut, or both may include a varus/valgus adjustment means for bending at least one of the upper and lower struts. The varus/valgus adjustment means may include a rotating gear component driving a linearly traversing component.

DETAILED DESCRIPTION OF THE PREFERRED EMBODIMENTS

Figures 1, 5:
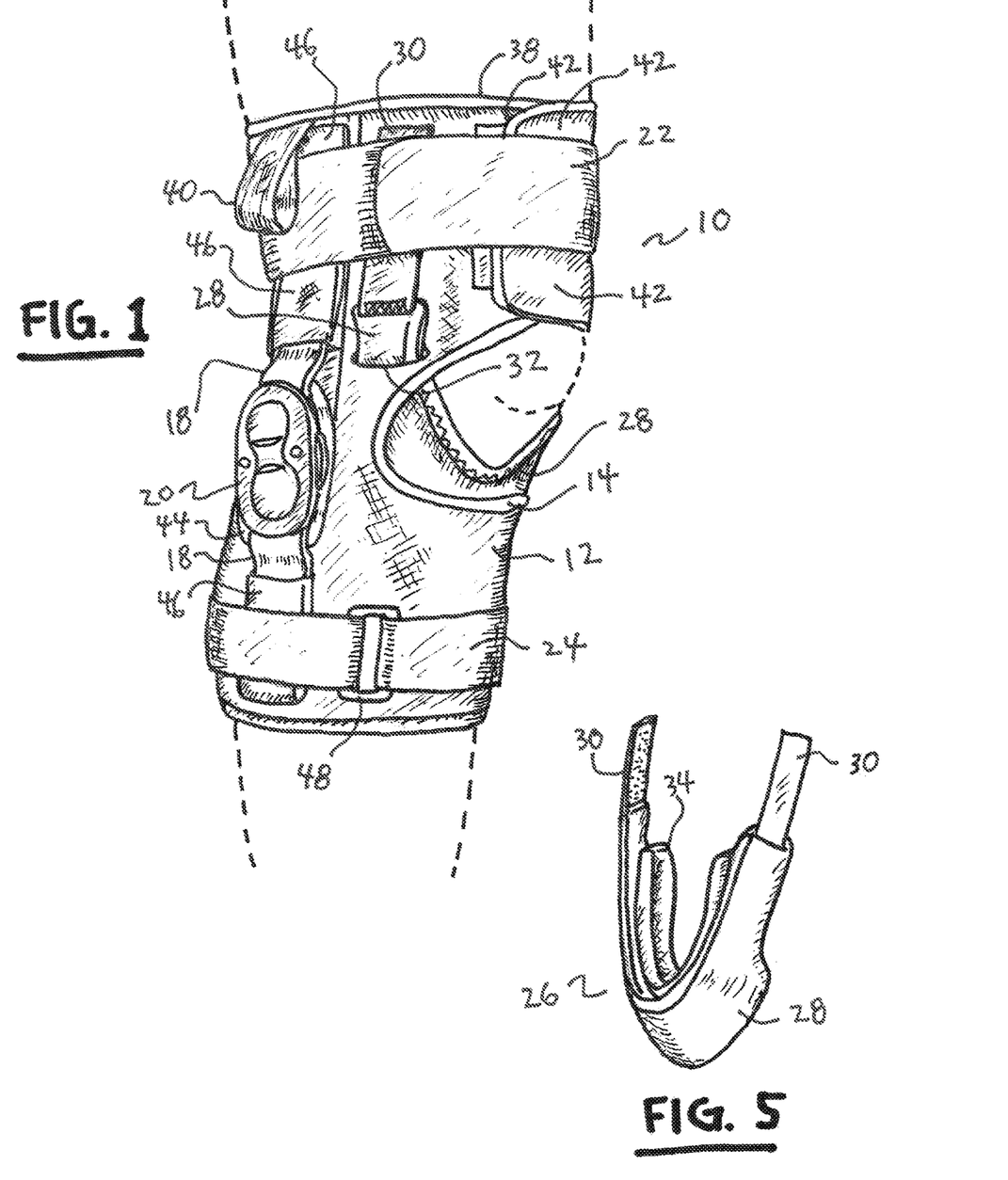
FIG. 1 is a perspective view of the lateral side of a preferred embodiment knee brace as worn on the right leg.
FIG. 5 is a perspective view of the patella support assembly.

FIG. 1 shows a preferred embodiment of the present invention osteoarthritis knee brace 10 as worn on the right leg of a patient. In this embodiment, the brace 10 is constructed from a tubular-shaped, elastic sleeve or wrap 12 that generally envelopes the knee joint and supports a portion of the upper leg and the lower leg. The sleeve 12 preferably includes a patella opening 14 to expose the patella to minimize skin chafing or wearer discomfort. At the medial and lateral sides of the sleeve 12 are respective stiffeners 16, 18. A hinge 20 is located on each stiffener 16, 18 at about a midpoint so that the stiffeners bend and follow the natural bend of the knee. The stiffeners 16, 18 allow the full flexion and extension range of motion for the knee joint while controlling adduction or abduction knee misalignment. The preferably metal stiffeners 16, 18 are attached to the sleeve 12 and are further retained to the upper and lower leg by use of an optional upper strap 22 and lower strap 24. The straps 22, 24 are preferably inelastic and fitted with hook and loop fasteners (e.g., Velcro®) to provide adjustability to fit the wearer's physique and achieve the desired pressure on the wearer's hamstring and calf.

Fitted inside the sleeve 12 is a generally U-shaped patella control assembly 26, shown in the perspective view of FIG. 5. The patella control assembly 26 preferably includes an adjustable patella sling or support 28 in the shape of a "U" or crescent terminating at opposite ends with attachment/pull strips 30. The U-shaped patella support 28 is preferably made from a stretchable, soft fabric such as neoprene. The pull strips 30 are preferably made from inelastic strips of material that have the hook portion of a hook and loop fastener.

The patella control assembly 26, and specifically the patella support 28, is preferably stitched, glued, welded, or similarly anchored at the base of the "U" to the interior of the sleeve 12 at about the patella opening 14 just beneath the knee joint. The patella support 28 and the sleeve 12 are joined together so that the knee brace 10 when applied by the patient or orthopedist is in one piece without loose parts. Also, the anchoring point ensures the patella support 28 is already positioned generally at the correct location relative to the knee joint without further adjustments. In alternative embodiments, the patella support 28 is not stitched or glued to the sleeve 12 as described above, but rather hangs freely and only from the pull strips 30.

As seen in FIG. 1, the pull strips 30 pass through slit-like openings 32 in the sleeve 12, which slits 32 lead from inside the sleeve to outside the sleeve, where on the outside of the sleeve, the wearer has easy access and can pull upward, at angle, or both, on the pull strips 30 to adjust the force and location of the support 28 against the patella. As described above, the base of the "U" of the patella support 28 is optionally anchored or otherwise stitched to the sleeve 12 near the opening 14 just beneath the knee. So tugging on the pull strips 30 tensions the elastic patella support 28 against the stationary anchor point, and stretches the patella support 28 around the patella for tight support. Once the wearer adjusts the patella support 28 to the desired tension, pressure, and location, she can attach or anchor the pull strips 30 to the exterior of the sleeve 12, which has a pile patch complement to a hook and loop fastener. The openings or slits 32 in the sleeve 12 are wide enough for easy sliding and passage of the pull strips 30. Furthermore, depending on how the individual pull strips 30 are adjusted by the wearer, it is possible that the patella support 28 apply a lateral or medial force component on the knee joint/patella in addition to the upward force. Adjusting the tension in the patella support 28 also adjusts the amount of force or pressure applied against the patella.

The arrangement of the patella control assembly 26 gives the wearer directional force applied to the patella when the wearer pulls on the pull strips 30 that are readily and conveniently accessible from the outside of the sleeve 12. That tension on the patella is maintained when the wearer anchors the pull strips 30 to the exterior of the sleeve 12. If during flexion of the knee the assembly 26 is perceived as uncomfortable or too tight, it is an easy "on the fly" adjustment for the wearer to slightly tension or release the pull strips 30 individually or in unison and re-anchor them to the sleeve 12. This adjustment is independent of the sleeve 12, which remains stationary. Thus, adjustment of the sleeve 12 and the patella support 28 can be achieved independently.

In FIG. 5, the patella control assembly 26 may include an optional, rubber-like patella buttress 34 also having a generally "U," "C," or like shape. The patella buttress 34 is glued, stitched, or fastened to the interior of the patella support 28 and is applied to the patella. The buttress 34 is preferably made from polyurethane, and may be made from felt, an elastomer, gel, or known rubber-like material, to act as a cushion for the wearer's comfort and to help stabilize the patella.

Figure 9:
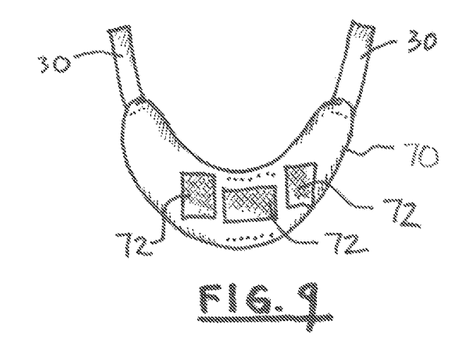
FIG. 9 shows an alternative embodiment patella support.

Other shapes for the patella support 28 are contemplated, including a semicircle, a curved strip, a trapezoid, etc., such that their form maximizes engagement and support for the patella. FIG. 9 shows an alternative embodiment patella support 70. It is shaped generally like the U-shape of the patella support 28 shown in FIG. 5, and has the two pull strips 30 that pass through the slits 32 in the sleeve as in the FIG. 5 embodiment. The shape of the patella support 28 is more of a crescent and slightly different from the FIG. 5 embodiment; the shape illustrates an alternative approach to capture or cup the patella.

FIG. 9 shows the interior surface of the patella support 70 that faces the wearer's knee. On that surface facing the knee are nodules, patches, or areas of a tacky material 72 such as silicone or urethane that is silk screened, deposited, or embedded thereon. The tacky material 72 helps the patella support 70 grip the skin of the wearer. The gel patella buttress 34 may thus be omitted.

Figure 2:
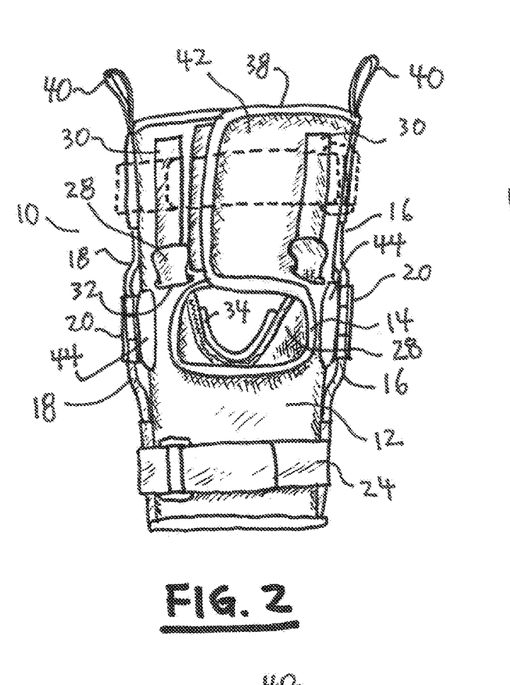
FIG. 2 is a front view of the knee brace from FIG. 1.
Figure 3:
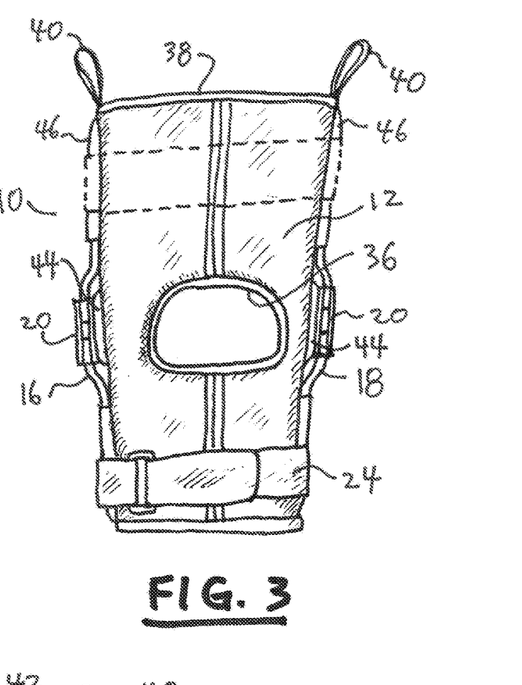
FIG. 3 is rear view of the knee brace from FIG. 1.
Figure 4:
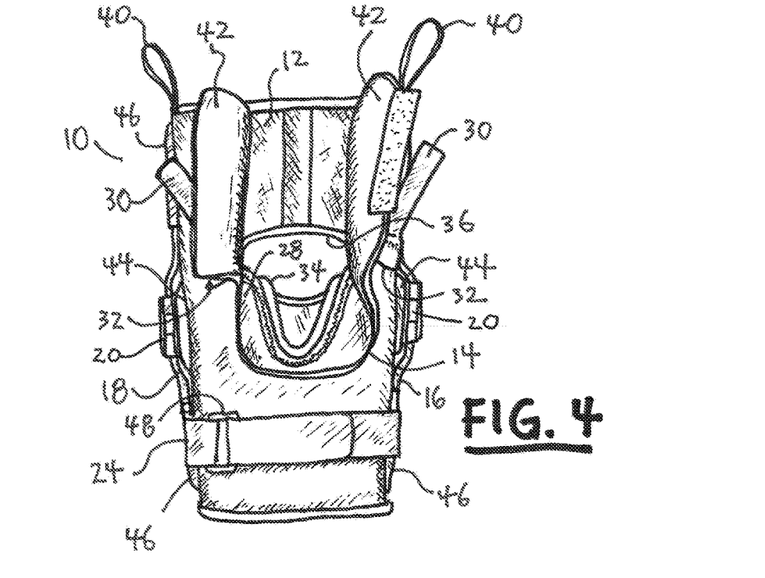
FIG. 4 is a front view of the knee brace with the top anterior portion of the sleeve having the flap closure swung open.

FIGS. 2 and 3 are a front/anterior view and a rear/posterior view, respectively, of the knee brace from FIG. 1. FIG. 4 is a front/anterior view of the sleeve 12 with the flap closure 42 swung open.

As seen in FIGS. 1-4, the sleeve 12 preferably covers the knee joint and portions of the upper and lower leg. The sleeve 12 is preferably made from an elastic, flexible, padded fabric sheet or sheets stitched together. The sheet material includes neoprene, and more preferably, includes an air mesh spacer fabric, which is lighter than neoprene, is more air permeable for wearer comfort, has strength but is stretchable, minimizes moisture and mold build up, etc. The sleeve 12 may be perforated to keep the wearer's leg cool. The exterior may include pile sections to facilitate attachment of the pull strips 30 and other hardware (e.g., straps, flaps) that use hook and loop fasteners.

The sleeve 12 includes the optional patella opening 14 and an optional popliteal or back-of-the-knee opening 36, offering more comfort, minimal bunching of the fabric, and better fitment for the wearer. The interior of the sleeve 12 may include a smooth nylon lining or the like for wearer comfort. The lining minimizes binding if the knee brace 10 is worn over clothing, and feels cool if touching skin.

The top 38 of the sleeve 12 may include optional pull up loops 40 to aid the wearer during application of the knee brace 10 to her limb. Furthermore, to ease the application of the brace, the preferred embodiment sleeve 12 includes upper closure flaps 42 on the anterior portion that swing open, as seen in FIG. 4. This permits easier passage of the wearer's foot and leg into the knee brace 10 when applying the brace, and insures easy removal of the brace 10. The flaps 42 are tensioned, overlap, and close together with hook and loop fasteners. Other closures known in the art are contemplated, including claws, buttons, D-rings, hooks, zippers, laces, straps, etc.

Figure 6:
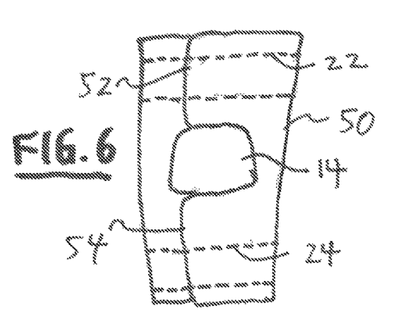
FIG. 6 is an alternative embodiment knee brace with upper and lower openings.

In FIG. 4, the flaps 42 swing apart to reveal the split opening that merges with the patella opening 14 of the sleeve 12. This combined open space creates a wider mouth to receive the wearer's foot and leg for easy passage through the tubular sleeve 12. FIG. 6 is a front elevational view of an alternative embodiment knee brace 50 similar in construction to that shown in FIGS. 1-4, except this embodiment includes optional upper and lower anterior openings 52, 54, above and beneath the patella opening 14. The openings 52, 54 are secured closed using, preferably, hook and loop fasteners. Other means for securing the flaps include zippers, laces, straps, hooks, and the like. The upper and lower straps are shown in dashed lines. The one or more sleeve opening(s) are preferably at the front/anterior, but may be located at the side/medial/lateral or at the back/posterior.

It is further contemplated in an alternative embodiment a knee brace that has an elastic sleeve that is tubular and does not have upper or lower anterior openings. The sleeve would be constructed as a soft, elastic tube. Without the anterior opening(s), no closure flaps are required.

Optional upper and lower straps 22, 24 are used to improve support and attachment of the knee brace 10 to the wearer. The preferred embodiment straps 22, 24 are inelastic, circumscribe the leg, with one end that passes through an optional D-ring 48 to flip over and anchor onto itself via hook and loop fasteners. Of course, more than the two straps 22, 24 shown in the drawings may be used, and one or more may be elastic. In FIGS. 2 and 3, the upper strap 22 is shown in dashed lines to better illustrate the other parts of the knee brace 10. In FIG. 4, the upper strap 22 has been removed for the sake of illustration.

The present invention knee brace 10 includes medial and lateral hinged stiffeners 16, 18. Each stiffener 16, 18 is preferably made of rigid metal or plastic bars that are hinged at about the midpoint. The hinge 20 includes intermeshing gear teeth to enable the bars to pivot. As such, the hinge 20 is polycentric with multiple pivot points to more closely follow the knee joint's natural range of motion. Optional condyle pads 44 may be included at the interior of the hinges 20 to improve wearer comfort. The condyle pads 44 contained soft, resilient padding (e.g., urethane foam, gel, etc.) material to minimize pressure on the medial and lateral sides of the wearer's knee. The stiffeners 16, 18 are positioned inside pockets that are stitched to the sleeve 12. Alternatively, the stiffeners 16, 18 may be embedded into the fabric of the sleeve.

Figure 7:
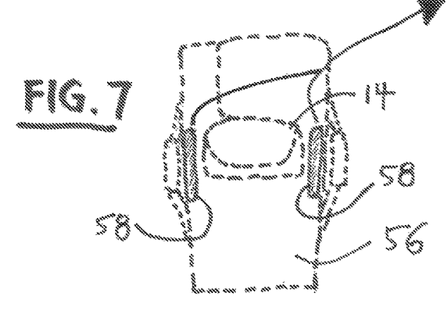
FIG. 7 shows an alternative embodiment knee brace fitted with internal condyle pads.
Figure 10:
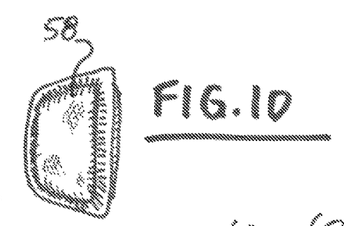
FIG. 10 is an exemplary embodiment of an internal condyle pad.

FIG. 7 is a front elevational view of an alternative embodiment knee brace 56 (shown in phantom lines) that is similar to the embodiment shown in FIGS. 1-4, but now includes an internal condyle pad 58 at the medial and lateral locations on either side of the wearer's knee. FIG. 10 provides a more detailed view of one internal condyle pad 58. Each internal condyle pad 58 is oversized and much larger than the external condyle pads 44 shown in FIG. 4. The external condyle pad 58 is preferably a pillow containing air cell, soft gel, Confor®, or like urethane foam. The Confor® foam provides soft padding for the arthritic and swollen knee and is resilient for impact protection. The pillow is covered front and back with a soft fabric and stitched around its periphery, then anchored into the interior of the sleeve by stitching, glue, mechanical fasteners, or the like.

Figure 8:
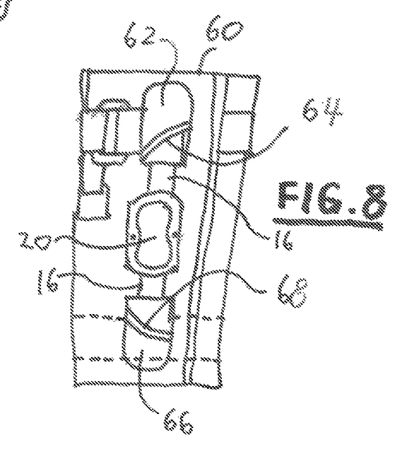
FIG. 8 shows an alternative embodiment knee brace having pull up pockets instead of loops.

FIG. 8 is a side elevational view of an alternative embodiment knee brace 60 similar to the embodiment of FIGS. 1-4, but with the pull up loops 40 at the top of the sleeve omitted. In their place (or in addition to) are finger access pockets 62, which are stitched to the sleeve exterior on three sides or mostly around its periphery of the pocket, leaving a finger accessible opening 64 on the fourth side facing the bottom of the sleeve. There is preferably one pocket on the lateral side and one on the medial side of the knee brace 60 near the top of the sleeve, and an optional pair at the bottom of the sleeve. The wearer of the knee brace 60 can insert his or her index or middle finger of each hand into the respective openings 64 and simultaneously pull upward thereby sliding the brace upward on the wearer's leg. At the bottom of the sleeve are an optional pair of pockets 66 on the medial and lateral sides, with upward facing finger openings 68. The wearer can insert his or her finger or thumb down into the openings 68 and push downward to slide the knee brace 60 downward on the leg. The pockets 64, 66 are generally, preferably aligned with the metal stiffeners 16, 18 and hinge 20 assembly at the medial and lateral sides of the knee brace. Thus, pulling on the pockets 64, 66 pulls the metal hardware assembly 16, 18, 20 along with the pockets to minimize chances of accidentally tearing the fabric or a seam. In yet another embodiment (not shown), the pockets 64, 66 may be replaced with low profile loops extending laterally from the sleeve surface. The loops provide finger or thumb access to hook on to for leverage to shift the knee brace up or down on the wearer's leg for improved fitment.

The present invention in an alternative embodiment is directed to a global unloader osteoarthritis brace. That is, the osteoarthritic brace is preferably designed to address substantially all symptoms of a classic unicompartmental or bicompartmental osteoarthritic knee.

Figures 11A, 11B:
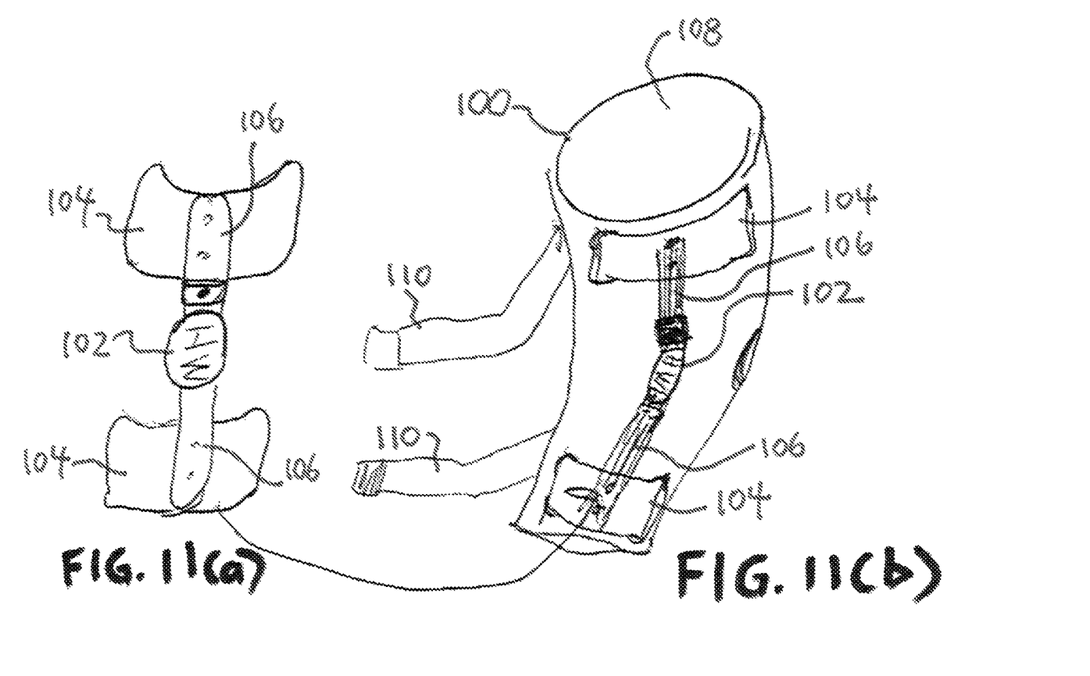
FIG. 11(a) is an alternative embodiment cuff and hinge.
FIG. 11(b) shows a knee brace with a single hinge.

This alternative embodiment global unloader knee brace 100 is shown in FIGS. 11(*a*) and 11(*b*). The brace 100 in the exemplary embodiment has the brace structure depicted in the prior embodiments of FIGS. 1-10, and now includes a single hinge 102, either having a range-of-motion limited or non-range of motion limited. Similar to the hinge 20 of prior embodiments (e.g., FIGS. 1-4), the hinge 102 has upper and lower stiffeners or struts 106 made of a preferably rigid metal (e.g., steel, aluminum), plastic, ceramic, or the like, and extending alongside the calf and thigh regions. The struts 106 have optional cuff attachments 104 generally aligning with the wearer's calf and thigh. The cuffs 104 are preferably slightly rigid and partially surround and cup the calf or thigh. In the preferred embodiment, either cuff 104 may be made from a pliable, bendable polymer or metal for improved fitment and leg support.

The exemplary embodiment brace 100 further contemplates that the single hinge 102 may be fitted to either the medial or lateral side of the brace 100 as determined by wearer or physician. To accommodate the medial or lateral attachment, the brace 100 includes, preferably strut pockets formed or stitched into the sleeve 108, similar to the FIG. 8 embodiment. The distal ends of the strut 106 fit inside the pockets. The struts 106 may also be attached to the sleeve 108 through other means known in the art, e.g., using hook-and-loop fasteners, straps, etc.

Figures 12, 13:
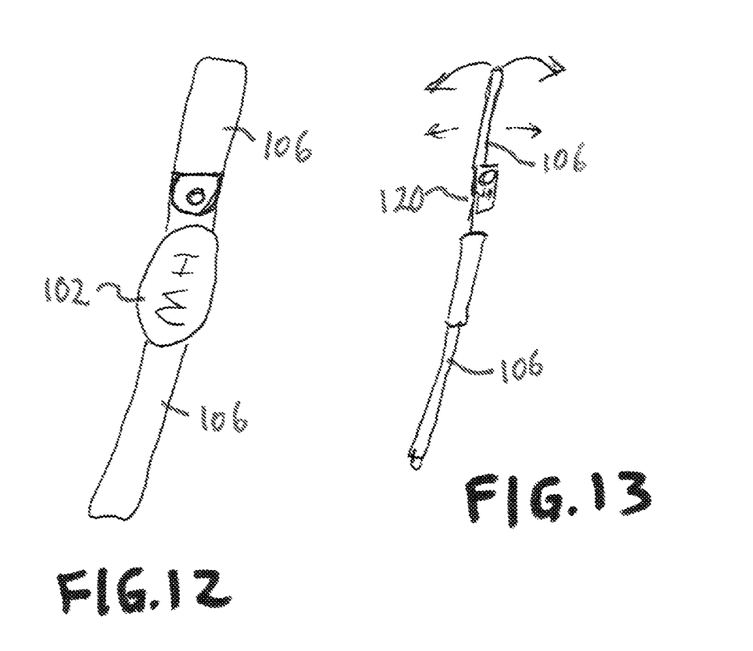
FIG. 12 shows an alternative embodiment varus/valgus knee adjustment hinge.
FIG. 13 is the FIG. 12 embodiment with a varus/valgus adjustment actuated with a worm shaft.
Figure 14A:
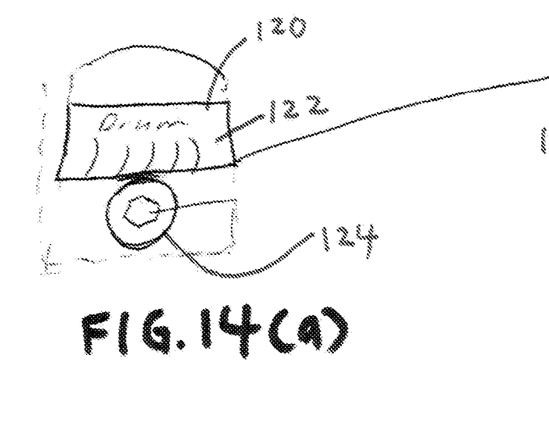
FIG. 14(a) is a magnified view of a varus/valgus adjustment using a worm shaft with rack or drum.
Figure 14B:
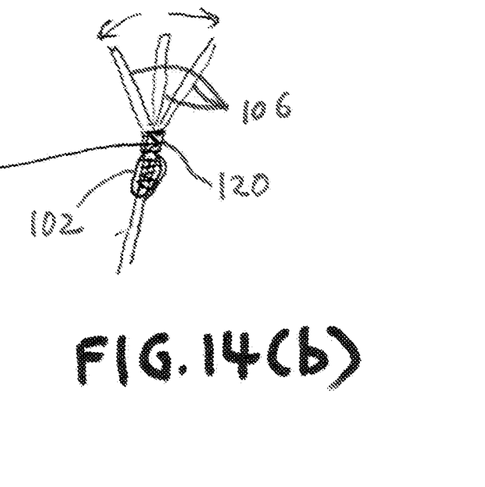
FIG. 14(b) indicates operation of the varus/valgus adjustment moving a strut in different directions.

The present invention alternative embodiment brace 100 to further enhance a universal set-up, the physician or wearer may configure the brace in a varus (i.e., bowlegged) or valgus (i.e., knock-kneed) arrangement used for a right leg or a left leg. FIG. 12 shows a hinge 102 that may be modified to include varus/valgus adjustments designed to better contour to the patient's leg, and to provide a varus or valgus push or pull to assist in unloading or opening the joint space on a unicompartmental osteoarthritic knee thus providing stability to the knee joint. The hinge 102 is shown without the optional cuffs 104. FIGS. 13, 14(*a*) and (*b*) show one preferred embodiment of a varus/valgus adjustment mechanism 120 attached to a strut 106 corresponding to the thigh/femur (adjustment to the calf/tibia strut is contemplated). In FIG. 14(*a*), the adjustment mechanism 120 includes a worm gear, drum, or rack 122 driven by a worm shaft 124. The worm gear, drum or rack 122 is affixed to the upper strut 106. The wearer twists on the worm shaft 124 via a knob or like grippable surface, rotating it clockwise or counterclockwise. The rotating worm shaft 124 moves the gear, drum, or rack linearly 122 to traverse along the teeth of the worm shaft 124. When the gear, drum or rack 122 moves linearly, it pulls or pushes the upper strut 106 based on clockwise or counterclockwise rotation of the worm shaft 124, slightly bending the strut 106.

In an alternative embodiment, a rack and pinion system or like conventional mechanism for translating rotational motion to linear motion is contemplated. Further, a worm gear can be actuated by the wearer to translate a worm shaft linearly to bend the strut.

FIGS. 13, 14(b) via the arrows indicate the directions of bend of the strut 106 out of neutral to more closely fit with the patient's varus or valgus misalignment. In the anterior/frontal views of FIGS. 13 and 14(b), if the hinge 102 is worn on the patient's left leg on the lateral side, the arrow pointed left indicates varus (bowlegged) adjustment while the arrow pointed right indicates valgus (knock-kneed) adjustment.

The brace 100 may optionally have an adjustable calf (or thigh) component that allows for a more customized fitment to a patient's conically-shaped leg. For example, in FIG. 15(a), the sleeve 108 may have anterior split openings at the calf 54, the thigh 52, or both. The upper and lower anterior openings 52, 54 are optionally closed by overlapping flaps at the calf, thigh (FIG. 2), or both (FIG. 6), where the overlap adjusts the diameter of the sleeve at the calf and/or thigh. Alternatively, in FIG. 15(a), either or both the upper and lower anterior openings 52, 54 maintain the open gaps between the flaps 118 when applied to the leg. The flaps 118 are held against the leg by the overlying, adjustable-length straps 110 (FIGS. 1, 11(b)) wrapping around the calf, thigh, or both. An alternative embodiment sleeve 108 has no upper anterior opening above the patella opening 14 and only a lower anterior opening 54 beneath the patella opening 14. This construction is depicted in FIG. 15(a) with dashed lines that represent the upper anterior opening 52 is omitted.

The calf (or thigh) adjustment thus allows the brace 100 to custom-fit a larger thigh and smaller calf (or vice versa) versus the pre-set range of sizes available with an off-the-shelf brace. Instead of a large thigh and a large calf within a normal size range, this adjustment allows the bridging of sizes to accommodate, e.g., a sized-small calf with a sized-large thigh, and hence, a wider range of patient leg shapes and sizes.

Figure 15A:
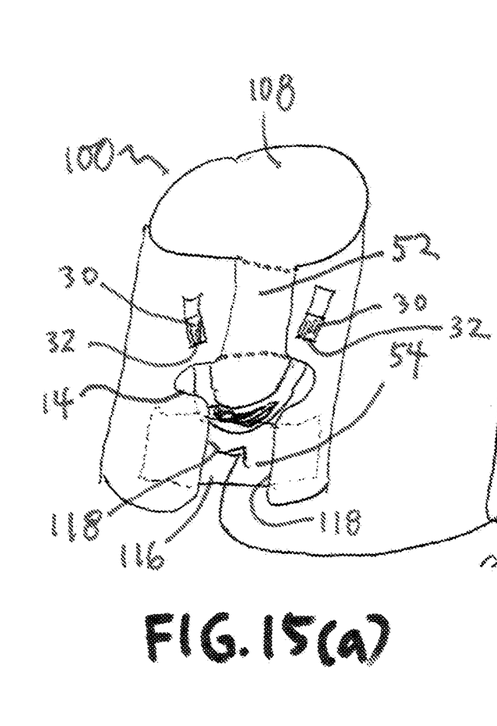
FIG. 15(a) is another alternative embodiment knee brace with a leg size adjustment using anterior openings at the calf, thigh, or both to fit a conical leg.
Figure 15B:
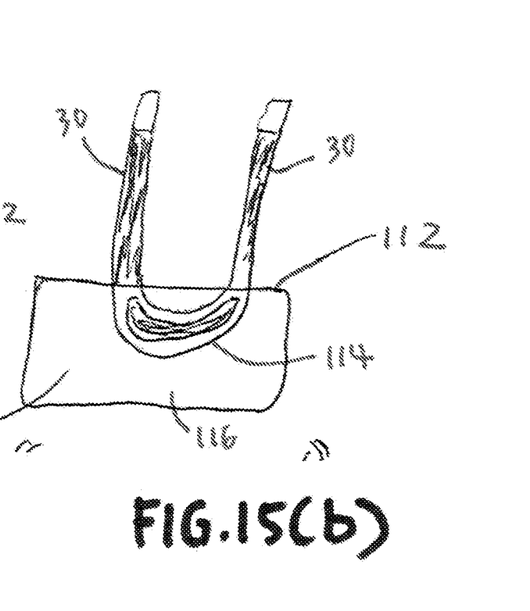
FIG. 15(b) is a magnified view of a sling with anchor fitted to the knee brace in FIG. 15(a).

Within the gap 54 beneath the patella is an optional patellar control sling 112 as shown in FIGS. 15(a) and 15(b) having a construction similar to the prior disclosed embodiments such as in FIG. 5. The sling has a U-shaped buttress 114 and pull strips 30. In FIG. 15(a), the pull strips 30 pass through slits 32 formed in the sleeve 108. The pull strips 30 extend upward toward the wearer's pelvis, through the slits 32, from the interior to the exterior of the sleeve 108. The distal ends of the pull strips 30 are exterior to the sleeve 108 to be easily accessible by the wearer for applying tension. Once tension is applied, the distal ends of the strips 30 are anchored via hook-and-loop fasteners to the exterior of the sleeve 108.

Consequently, the U-shaped buttress 114 lifts and controls the patella with an inferior to superior directional pull. The buttress 114, located at the interior of the sleeve 108, supports the bottom of the patella. The wearer can easily tug on the distal ends of the pull strips 30 to apply an upward (toward the pelvis) force on the patella via the buttress 114, urging it in the same direction. As the wearer walks, jogs, or moves about, his or her patella is maintained in the same position relative to the upper and lower leg due to this upward (i.e., toward the pelvis) lifting pressure. Osteoarthritic knee pain to the wearer is thus minimized or eliminated.

In FIG. 15(b), the bottom buttress 114 of the U-shape sling 112 has an anchor or patch 116 integrated or stitched to the sling 112. The anchor 116 is preferably padded, is somewhat rigid to retain its general rectangular shape, and has some thickness for cushioning. The anchor 116 rides against the leg, is held there by the overlying calf strap 110, which also places the flaps 118 freely against the anchor 116 as in FIG. 15(a). Optionally, the flaps 118 may be attached to the anchor 116 by hook-and-loop fasteners. Further optionally, the buttress 114 may be stitched or bonded to the sleeve 108 just beneath the patella opening 14.

Thus, the present embodiment osteoarthritis brace 100 is like no other "unloader" or "off-loader" brace in the market, and addresses both joint space pain with a varus/valgus adjusting hinge 102 or shaped unloading hinge, but also addresses patella femoral pain syndrome through the patella sling 112.

In alternative embodiments, the brace 100 may adopt a pull up style where the sleeve is a tapered elastic tube with only a patella opening and no upper or lower anterior openings as in FIG. 11(b); a wrap-around style sleeve as depicted in FIG. 6, or a hybrid of the two sleeve as shown in FIG. 1. The brace 100 is prefabricated and can be issued to the patient as an Off-The-Shelf (OTS) item, or custom-fitted to the patient by bending, trimming, or molded by a trained professional or physician.

In still another alternative embodiment, the osteoarthritis knee brace 100 includes dual hinges 102 with one stationed on the lateral side and one on the medial side. This osteoarthritis knee brace is designed to address all symptoms of a classic bicompartmental and even tricompartmental osteoarthritic knee.

While particular forms of the invention have been illustrated and described, it will be apparent that various modifications can be made without departing from the spirit and scope of the invention. Furthermore, components from one embodiment may be modified or combined with the components from another embodiment.

What is claimed is:

1. An osteoarthritis knee brace for lifting a wearer's patella, comprising:
   a flexible and elastic sleeve having a tubular shape with an interior and exterior, lateral and medial surfaces, the sleeve further having a patella opening at an anterior surface, and a plurality of slits;
   wherein the sleeve includes an anterior split opening at least one of above and below the patella opening;
   a hinge having upper and lower struts fitted to the sleeve;
   a flexible patella support having elongated strips extending therefrom, wherein the patella support is positioned in the interior of the sleeve beneath with the patella opening, and wherein the elongated strips pass from the interior of the sleeve through the slits to the exterior of the sleeve, and further extend upward to be adjustably anchored to the sleeve above the patella opening, and wherein pulling on the elongated strips adjusts the patella support to lift the patella; and
   a strap extending circumferentially around the outside of the sleeve.

2. The osteoarthritis knee brace of claim 1, wherein at least one of the upper strut and the lower strut includes a varus/valgus adjustment means for bending at least one of the upper and lower struts.

3. The osteoarthritis knee brace of claim 2, wherein the varus/valgus adjustment means includes a rotating gear component driving a linearly traversing component.

4. The osteoarthritis knee brace of claim 2, wherein the varus/valgus adjustment means includes a rack and pinion.

5. The osteoarthritis knee brace of claim 1, wherein the patella support includes an anchor disposed at the anterior opening below the patella opening.

6. The osteoarthritis knee brace of claim 5, wherein the sleeve at the anterior opening includes flaps that at least partially overlie the anchor.

7. The osteoarthritis knee brace of claim 5, wherein the anchor includes padding and a rectangular shape.

8. The osteoarthritis knee brace of claim 1, wherein the patella support is not attached to the sleeve.

9. The osteoarthritis knee brace of claim 1, wherein the knee brace includes two hinges with respective upper and lower struts, the two hinges disposed respectively on the lateral and medial surfaces of the brace.

10. An osteoarthritis knee brace for lifting a wearer's patella, comprising:
a flexible and elastic sleeve having a tubular shape with an interior and exterior, lateral and medial surfaces, the sleeve further having a patella opening at an anterior surface, and a plurality of slits above the patella opening;
wherein the sleeve includes an anterior opening at least one of above and below the patella opening;
a hinge having an upper strut and a lower strut fitted to the sleeve;
a flexible patella support having elongated strips extending therefrom, wherein the patella support is positioned in the interior of the sleeve proximate with the patella opening, and wherein the elongated strips pass from the interior of the sleeve through the slits to the exterior of the sleeve, and further extend upward to be adjustably anchored to the sleeve above the patella opening, and wherein pulling on the elongated strips adjusts the patella support to lift the patella; and
a strap extending circumferentially around the outside of the sleeve.

11. The osteoarthritis knee brace of claim 10, wherein at least one of the upper strut and the lower strut includes a varus/valgus adjustment means for bending at least one of the upper and lower struts.

12. The osteoarthritis knee brace of claim 11, wherein the varus/valgus adjustment means includes a rotating gear component driving a linearly traversing component.

13. The osteoarthritis knee brace of claim 10, wherein the patella support includes a padded anchor positioned underneath the patella.

14. The osteoarthritis knee brace of claim 10, wherein the knee brace includes two hinges fitted to the lateral and medial surfaces of the sleeve, respectively.

15. The osteoarthritis knee brace of claim 10, wherein the sleeve includes only an anterior opening below the patella opening.

16. An osteoarthritis knee brace for lifting a wearer's patella, comprising:
a flexible and elastic sleeve having a tubular shape with an interior and exterior, lateral and medial surfaces, the sleeve further having a patella opening at an anterior surface, and a plurality of slits above the patella opening;
a hinge having an upper strut and a lower strut fitted to the sleeve;
a flexible patella support having elongated strips extending therefrom, wherein the patella support is positioned in the interior of the sleeve proximate with the patella opening, and wherein the elongated strips pass from the interior of the sleeve through the slits to the exterior of the sleeve, and further extend upward to be adjustably anchored to the sleeve above the patella opening, and wherein pulling on the elongated strips adjusts the patella support to lift the patella; and
a strap extending circumferentially around the outside of the sleeve.

17. The osteoarthritis knee brace of claim 16, wherein the sleeve includes an anterior opening located at least one of above and below the patella opening.

18. The osteoarthritis knee brace of claim 16, wherein at least one of the upper strut and the lower strut includes a varus/valgus adjustment means for bending at least one of the upper and lower struts.

* * * * *